(12) United States Patent
White et al.

(10) Patent No.: US 7,740,074 B2
(45) Date of Patent: *Jun. 22, 2010

(54) TREE MOUNTED WELL FLOW INTERFACE DEVICE

(75) Inventors: Paul W. White, Banchory (GB); Paul F. Milne, Aberdeen (GB); Norman Brammer, Aberdeen (GB)

(73) Assignee: Vetco Gray Inc., Houston, TX (US)

( * ) Notice: Subject to any disclaimer, the term of this patent is extended or adjusted under 35 U.S.C. 154(b) by 818 days.

This patent is subject to a terminal disclaimer.

(21) Appl. No.: 11/595,444

(22) Filed: Nov. 9, 2006

(65) Prior Publication Data

US 2007/0144743 A1 Jun. 28, 2007

Related U.S. Application Data

(63) Continuation of application No. 10/972,061, filed on Oct. 22, 2004, now Pat. No. 7,201,229.

(60) Provisional application No. 60/513,294, filed on Oct. 22, 2003.

(51) Int. Cl.
*E21B 7/12* (2006.01)

(52) U.S. Cl. ................. 166/347; 166/336; 166/360; 166/368; 166/250.01

(58) Field of Classification Search ............ 166/347, 166/350, 360, 368, 340, 344, 345, 68.5, 250.01, 166/336
See application file for complete search history.

(56) References Cited

U.S. PATENT DOCUMENTS 2,233,077 A 2/1941 Gillespie et al.
2,790,500 A 4/1957 Jones
4,099,583 A * 7/1978 Maus ............................ 175/7
4,291,772 A * 9/1981 Beynet ......................... 175/5
4,813,495 A * 3/1989 Leach .......................... 175/6
5,280,766 A * 1/1994 Mohn ......................... 166/368
5,971,077 A * 10/1999 Lilley ......................... 166/368
6,457,529 B2 * 10/2002 Calder et al. ................ 166/368

(Continued)

FOREIGN PATENT DOCUMENTS

WO WO 00/70185 11/2000
WO WO 02/38912 A1 5/2002

*Primary Examiner*—Thomas A Beach
(74) *Attorney, Agent, or Firm*—Bracewell & Giuliani

(57) ABSTRACT

A subsea production tree has an external annular profile formed on an upper portion of the tree. A vertical passage extending from a lower end of the tree to an upper end of the tree for communicating with a string of tubing extending into the well. A lateral passage in the tree extending from the vertical passage. A flow path in fluid communication with the lateral passage extends laterally from the tree, the flow path having an upward facing receptacle. An adapter lands on the upper portion of the tree and connects to the profile, the adapter having a passage that registers with the vertical passage of the tree while the adapter lands on the tree. A flow interface device mounts to and lands with the adapter, the flow interface device having an inlet conduit and an outlet conduit, one of the conduits being connected to the passage in the adapter, the other of the conduits stabbing into sealing engagement with the receptacle as the adapter lands on the tree.

13 Claims, 3 Drawing Sheets

U.S. PATENT DOCUMENTS

| | | |
|---|---|---|
| 6,457,530 B1 | 10/2002 | Lam et al. |
| 6,460,621 B2 * | 10/2002 | Fenton et al. .............. 166/347 |
| 6,651,745 B1 * | 11/2003 | Lush et al. ................. 166/357 |
| 6,698,520 B2 | 3/2004 | Fenton et al. |
| 6,823,941 B2 | 11/2004 | Donald |
| 6,851,444 B1 * | 2/2005 | Kohl et al. .................. 137/13 |
| 6,966,383 B2 | 11/2005 | Milberger et al. |
| 7,210,530 B2 * | 5/2007 | Lush et al .................. 166/357 |
| 7,270,185 B2 * | 9/2007 | Fontana et al. ............. 166/358 |
| 7,569,097 B2 * | 8/2009 | Campen et al. ............... 95/243 |
| 7,647,974 B2 * | 1/2010 | Fenton ...................... 166/368 |
| 2005/0028984 A1 | 2/2005 | Donald et al. |

* cited by examiner

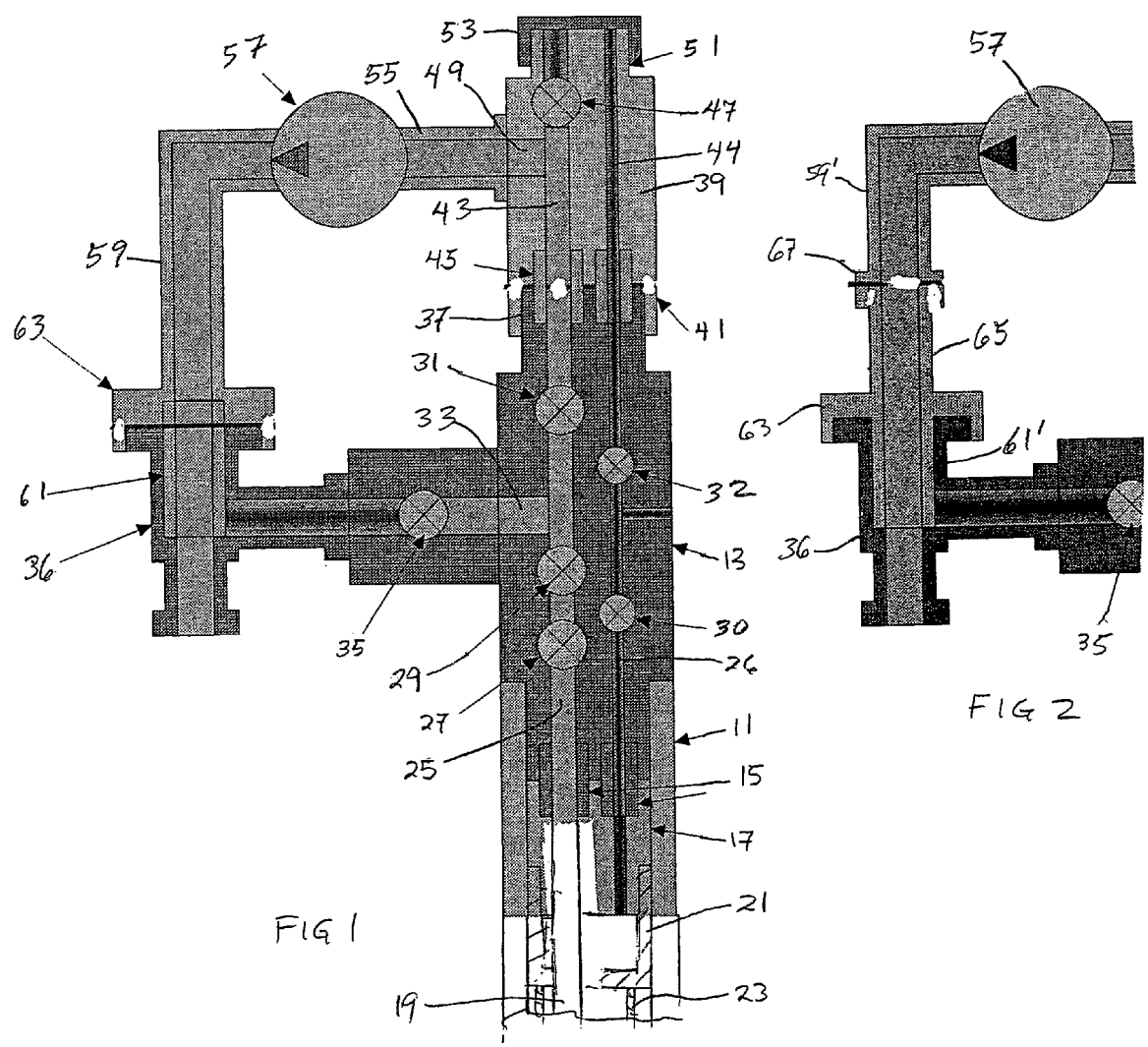

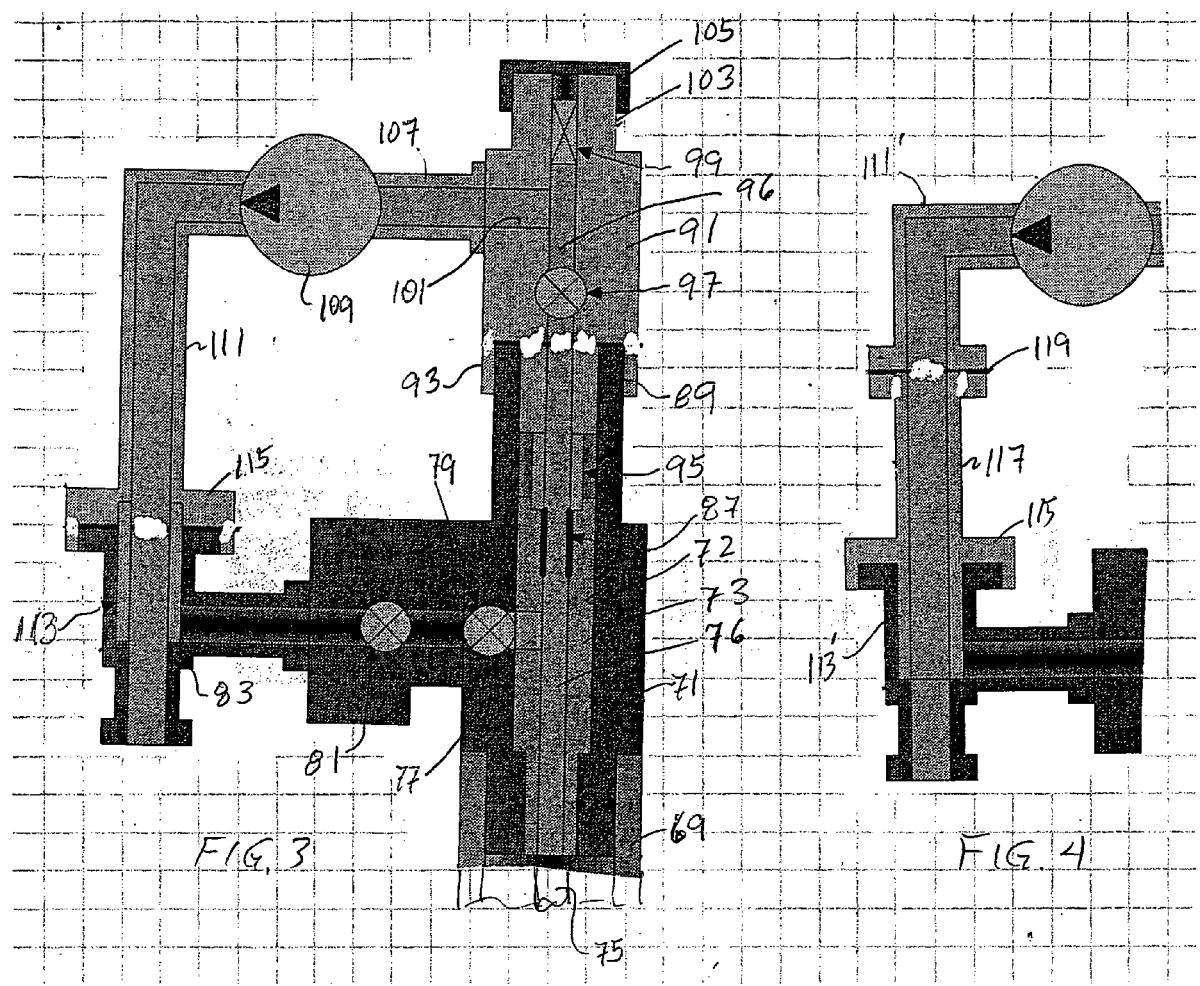

TREE MOUNTED WELL FLOW INTERFACE DEVICE

CROSS-REFERENCE TO RELATED APPLICATIONS

This application is a continuation of Ser. No. 10/972,061, filed Oct. 22, 2004, which claims priority to U.S. provisional patent application 60/513,294, filed Oct. 22, 2003.

FIELD OF THE INVENTION

This invention relates in general to subsea well assemblies, and in particular to a mounting apparatus for a well flow interface device, such as a subsea well pressure intensifier for boosting the well flow or for fluid injection.

BACKGROUND OF THE INVENTION

In one type of offshore well production, a subsea production tree is installed at the sea floor. The tree may be connected by a flowline jumper to a subsea manifold, which is connected to other subsea trees in the vicinity. A production riser may extend from the subsea manifold or from an individual tree to a processing facility, normally a floating platform. The well formation pressure is normally sufficient to cause the well fluid to flow up the well to the tree, and from the tree to the processing facility.

In very deep water, the well may have sufficient pressure to cause the well fluid to flow to the tree but not enough to flow from the sea floor to the processing facility. In other cases, the well may even lack sufficient pressure to flow well fluid to the sea floor. Downhole electrical submersible pumps have been used for many years in surface wells, but because of periodic required maintenance, are not normally employed downhole in a subsea well. A variety of proposals have been made for booster pumps to be installed at the sea floor to boost the well fluid pressure. However, because of the pump size, installation expense and technical difficulties, such installations are rare.

SUMMARY OF THE INVENTION

The subsea well assembly of this invention has a subsea production tree. A subsea pressure intensifier is carried by the tree in a manner such that the tree supports the weight of the intensifier. The tree has an external annular profile formed on an upper portion of the tree. An adapter lands on the upper portion of the tree and connects to the profile. The pressure intensifier is mounted to the adapter. The tree has a vertical production passage extending to an upper end, and the pressure intensifier is preferably laterally offset from the vertical production passage to enable access to the vertical production passage.

In the preferred embodiment, a flow line extends from the tree, the flow line having an upward facing receptacle adjacent the tree. A conduit extends from the pressure intensifier into engagement with the receptacle. A passage extends from a lower end of the tree to an upper end of the tree for communicating with a string of tubing extending into the well. The pressure intensifier is in fluid communication with the passage.

BRIEF DESCRIPTION OF THE DRAWINGS

FIG. 1 is a schematic view of a subsea well assembly having a mounting apparatus in accordance with this invention.

FIG. 2 is a partial view of the well assembly of FIG. 1, showing an alternate arrangement of the mounting apparatus of FIG. 1.

DETAILED DESCRIPTION OF THE INVENTION

Figure 5:
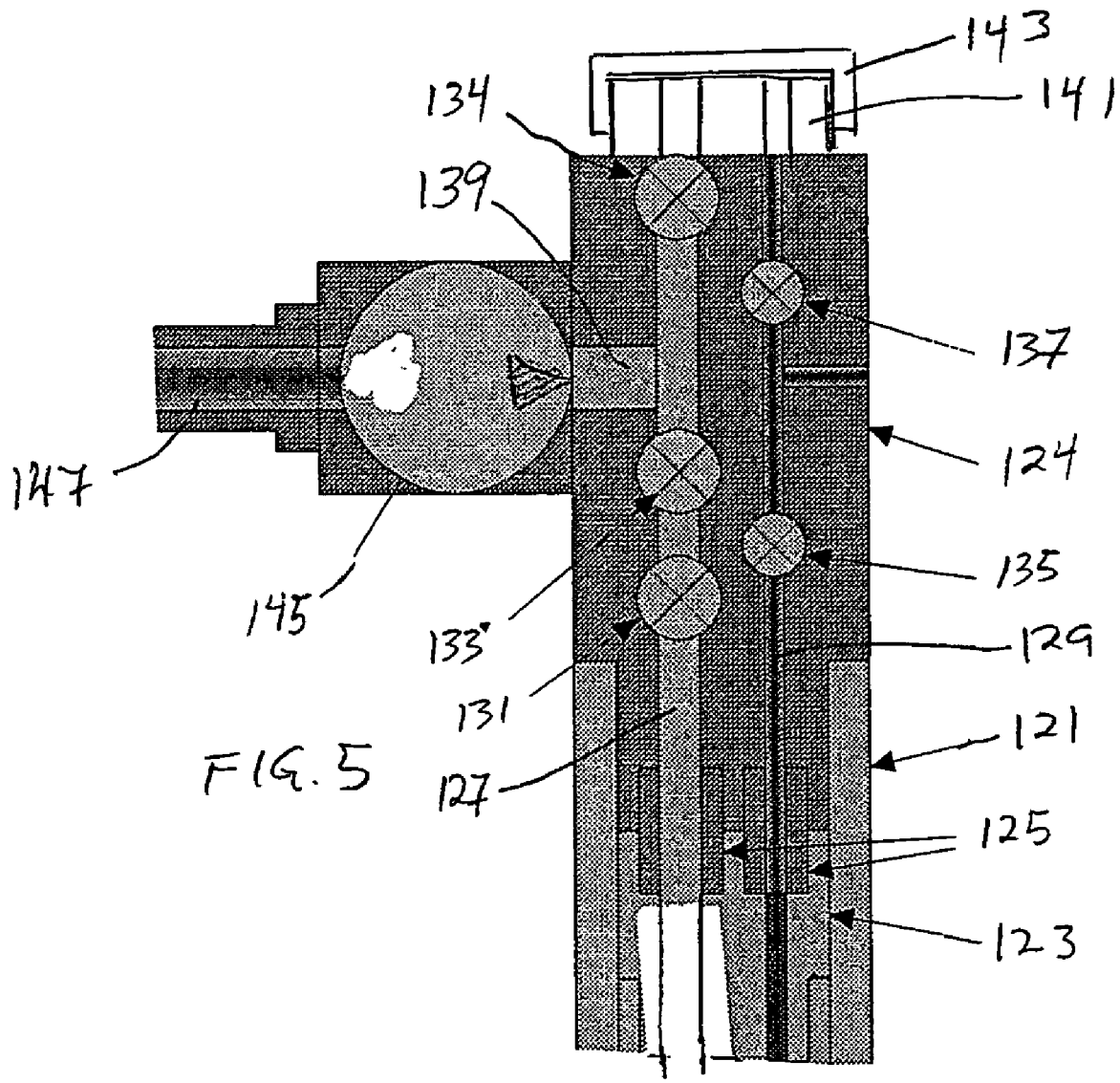
FIG. 5 is a schematic view of another embodiment of a subsea well assembly having a mounting apparatus in accordance with this invention.

Referring to FIG. 1, a wellhead housing 11 is located at the upper end of a subsea well. Wellhead housing 11 is a large tubular member mounted to a conductor pipe that extends to a first depth in the well. A subsea Christmas or production tree 13 is secured to the upper end of wellhead housing 11 by a conventional connector. In this embodiment, tree 13 has isolation tubes 15 that extends downward into sealing engagement with the production and annulus bores of a tubing hanger 17. Tubing hanger 17 supports a string of production tubing 19 that extends into the well and is located sealingly in wellhead housing 11. At least one casing hanger 21 is supported in wellhead housing 11, each casing hanger 21 being secured to a string of casing 23 that extends into the well and is cemented in place.

Tree 13 has an axially extending production bore 25 that communicates with one isolation tube 15 and extends upward through the tree. An annulus bore 26 communicates with the other isolation tube 15 and extends through tree 13 for communicating the annulus surrounding tubing 19. Production bore 25 has at least one and preferably two master valves 27, 29. Annulus valves 30, 32 are conventional located in annulus bore 26. A swab valve 31 is typically located in production bore 25 near the upper end of tree 13. A production port 33 extends laterally outward form production bore 25 and joins a production wing valve 35. Typically, production wing valve 35 is connected to a choke body 36 constructed for receiving a choke insert (not shown).

Tree 13 also has a mandrel 37 integrally formed on its upper end. Mandrel 37 comprises an annular profile such as a set of exterior grooves for connection to an adapter 39. Adapter 39 is a tubular member that has a connector 41 that engages mandrel 37. Connector 41 is of a conventional type such as used for connecting tree 13 to wellhead housing 11. Normally this type of connector is hydraulically actuated.

Adapter 39 has a production bore 43 that extends through it coaxially in alignment with production passage 25 in tree 13 and, in this embodiment, an annulus bore 44 that is coaxially aligned with tree annulus bore 26. Seal subs 45 extend between the production passages 43, 25 and the annulus passages 26, 44. Production bore 43 has an isolation valve 47. A production port 49 extends laterally from production bore 43 between isolation valves 45 and 47. Adapter 39 also may have a reentry mandrel 51 on its upper end, which has a profile that is similar to or the same as the profile of mandrel 37. A cap 53 is shown located on reentry mandrel 51 in this example.

Adapter 39 is employed to mount a flow interface device to tree 13. The flow interface device is typically a large, heavy unit that must be retrieved from time-to-time for repair or replacement. For example, the flow interface device could be a multi-phase flow meter or a pump or compressor (hereinafter referred to collectively as "pressure intensifier"). An inlet conduit 55 connects to production port 49. A subsea pressure intensifier 57 is mounted to inlet conduit 55. Pressure intensifier 57 may be of various types, but preferably is capable of pumping liquid having a significant gas content for boosting the pressure of the fluid flowing from tree 13. Pressure intensifier 57 could be a pump for injecting water into tree 13. Pressure intensifier 57 could also be a compressor for compressing gas supplied to it for introducing into the well to provide a gas lift. In the preferred embodiment, pressure intensifier 57 is electrically driven, thus its motor will also be incorporated with it and mounted to inlet conduit 55. Inlet conduit 55 may be very short, such that pressure intensifier 57 is essentially mounted to adapter 39. A conventional pressure intensifier 57, including its motor, controls and accessories, might weigh 15 tons, thus it is desired to position pressure intensifier 57 as close as possible to the axis of tree 13. The accessories might include a surge tank. However, in order to maintain vertical access to tubing 19, pressure intensifier 57 is not located on the vertical axis of passage 25, rather it is offset to one side.

The outlet of pressure intensifier 57 connects to an outlet conduit 59. Outlet conduit 59 has a downward extending portion with a tubular seal sub 61 that is in stabbing and sealing engagement with the bore in choke body 36. Preferably outlet conduit 59 is slightly flexible or compliant for stabbing seal sub 61 into choke body 36. A connector 63 connects outlet conduit 59 to choke body 36. Connector 63 is preferably a type that is remotely actuated with the assistance of an ROV (remote operated vehicle).

In one type of operation of the FIG. 1 embodiment, the reservoir formation pressure is initially sufficient to cause well fluid to flow from tree 13 into a production facility normally at the surface of the water. When operated in this manner, adapter 39, pressure intensifier 57 and conduits 55, 59 would not normally be located on subsea tree 13. Instead, a debris cap or a tree cap would be mounted to mandrel 37 of tree 13. Choke body 36 would have a choke insert for setting a desired flow rate of production fluid. Swab valve 31 would be closed and valves 27, 29 and 35 opened. The production fluid would flow up tubing 19, up production bore 25, and out through wing valve 35 and the choke contained within choke body 36.

When the well pressure decreases to a point that it lacks adequate pressure to flow fluid to the surface, the operator would close valves 27, 29, 31 and 35 and remove the tree cap or debris cap 53. The operator removes the choke insert from choke body 36. The operator then lowers into the sea the subassembly comprising adapter 39, pressure intensifier 57 and conduits 55, 59. Preferably the assembly is lowered on a lift line. With the assistance of an ROV, the operator connects adapter 39 to mandrel 37 and stabs seal sub 61 sealingly into choke body 36. The operator uses the ROV to connect connector 63 to choke body 36. A downward force due to the weight of pressure intensifier 57 passes through adapter 39 and tree 13 into wellhead housing 11. Preferably, no component of the downward force due to the weight of pressure intensifier 57 passes to choke body 36.

Once in place, the operator opens valves 27, 29, 31 and 45, and closes production wing valve 35, which causes flow to intake conduit 55. Pressure intensifier 57 operates to pump well fluid through choke body 36 to a production flow line. A choke insert is not required when operating pressure intensifier 57. Conduits 59, 55, pressure intensifier 57 and adapter passage 43 define a bypass flow path for well fluid flowing through vertical passage 25. The main flow, which is defined by production port 33 and production wing valve 33 is blocked by the closure of production wing valve 33.

Pressure intensifier 57 could also be employed with a well that had a downhole electrical pump suspended on the lower end of tubing 19. In that instance, the downhole pump would lift the well fluid to the upper end of tree 13, and pressure intensifier 57 would boost the pressure sufficiently to flow the well fluid to sea level. If the well is to be used for injecting fluid into the earth formation, the flow would be in reverse. Pressure intensifier 57 would be pumping fluid down tubing 19.

In some instances, adapter 39 and pressure intensifier 57 would be installed with tree 13 when tree 13 is initially being installed. This could be a case where it was known that the well fluid would have to be pumped or boosted from the production tree. Alternately, it could be when a new injection well is being completed. In these cases, a choke is not needed initially. Consequently, rather than a choke body 36, a simple T-conduit or some other arrangement could be utilized.

If it is necessary to remove pressure intensifier 57 for maintenance, the operator closes valves 27, 29 and 31 and disconnects adapter 39 from mandrel 37. The operator disconnects connector 63 from choke body 36. The operator then retrieves the assembly of adapter 39, pressure intensifier 57 and conduits 55, 59. After repair or replacement, the operator lowers the assembly and reconnects it in the same manner.

For various reasons, it may be desirable to run instruments and tools by coiled tubing or wireline into production tubing 19. This can be done without removing pressure intensifier 57 by removing debris cap 53 from adapter 39 and connecting a riser to adapter mandrel 51. With valves 27, 31, 45 and 47 open, the wireline or coiled tubing tools and instruments can be lowered through the riser and into tubing 19.

FIG. 2 shows an alternate embodiment of a portion of the assembly of FIG. 1. In FIG. 1, each time pressure intensifier 57 is lowered into engagement with tree 13, seal sub 61 must sealingly engage with the bore of choke body 36. This requires precision alignment and handling to avoid damaging the sealing surfaces. In FIG. 2, seal sub 61' remains in sealingly engagement with choke body 36 after the first installation. Seal sub 61' has a seal sub extension 65 that extends upwardly and terminates in a connector 67. Outlet conduit 59' has a mating end that connects to a connector 67. Connector 67 is a conventional subsea pipe connector that does not require a seal sub for sealing into a bore of a mating connector member.

In the embodiment of FIG. 2, when retrieving pressure intensifier 57, connector 63 remains connected. Connector 67 is released with the assistance of an ROV when retrieving the assembly and reconnected when returning the assembly. Because connector 67 does not need a seal sub, precision guidance is not required with each re-connection as in the first embodiment.

Figure 3:
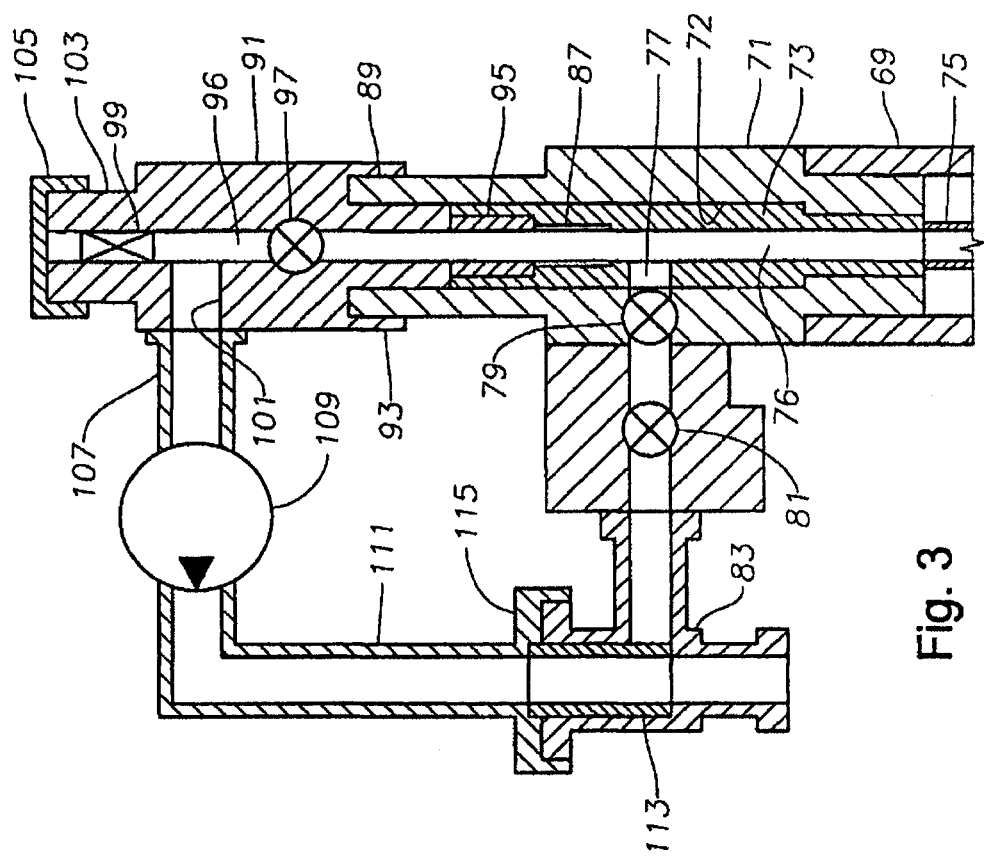
FIG. 3 is a schematic of another alternate embodiment of a subsea well assembly having a mounting apparatus in accordance with this invention.
Figure 5:
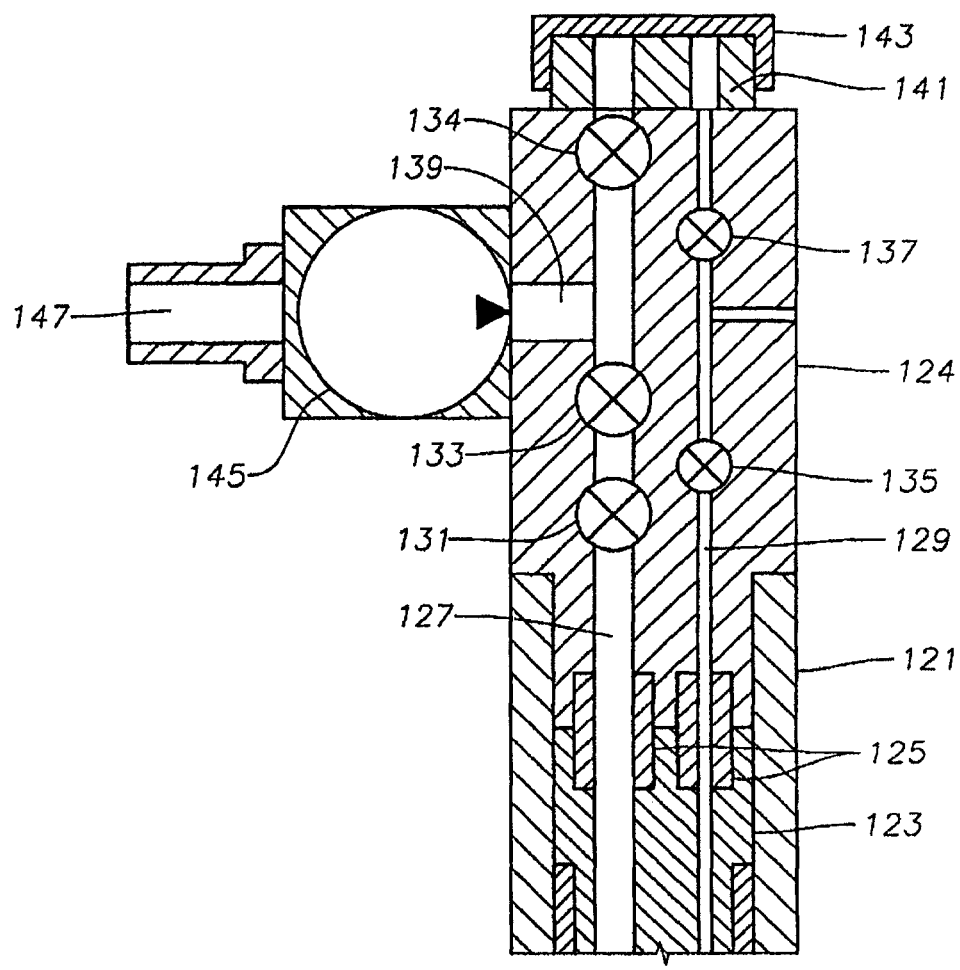

FIG. 3 shows the invention as applied to a different type of production tree 71, known as a horizontal or spool tree. Wellhead housing 69 is basically the same as the in the first embodiment. Tree 71, however, has a bore 72 that contains a tubing hanger 73. In the first embodiment, tubing hanger 17 is located within wellhead housing 11 rather than in tree 13. Tubing hanger 73 supports a string of tubing 75 that extends into the well for the flow of production fluid. Tubing 75 registers with a production passage 76 that extends through tubing hanger 73. A lateral production port 77 extends from production passage 76 through a production master valve 79 within tree 71. A production wing valve 81 is mounted to production master valve 79. Production wing valve 81 connects to a choke body 83, which in some cases could be a T-conduit, as discussed in connection with the first embodiment.

Production passage 76 of tubing hanger 73 has a crown plug profile 87 located above lateral production port 77. Profile 87 is adapted to receive a plug normally lowered and retrieved by a wireline. Tree 71 has a mandrel 89 on its upper end containing an external grooved profile. An adapter 91 lands on tree 71. Adapter 91 has a conventional hydraulically actuated connector 93 for connecting to tree mandrel 89. Adapter 91 has a seal sub 95 that extends downward into sealing engagement with production passage 76 in tubing hanger 73. Adapter 91 has a production passage 96 that registers with seal sub 95 for the flow of production fluid. An isolation valve 97 and a retrievable plug 99 are located within production bore 96. A swab valve could be used in lieu of plug 99.

A lateral production port 101 extends from production bore 96 between valve 97 and plug 99. Adapter 91 preferably has a mandrel 103 on its upper end that receives a debris cap 105. Lateral production port 101 connects to an intake conduit 107. A flow interface device, such as a subsea pressure intensifier109, is connected to intake conduit 107, which is preferably shorter than it appears in the drawing. Outlet conduit 111 is connected to the outlet of pressure intensifier109. Outlet conduit 111 has a downward extending portion with a seal sub 113. Seal sub 113 stabs sealingly into choke body 83. Connector 115 connects outlet conduit 111 to choke body 83.

In the operation of the embodiment of FIG. 3, typically, the well would initially be producing with sufficient pressure to flow well fluid to a surface processing facility. In such case, adapter 91, pressure intensifier109 and its conduits 107, 111 would not be located subsea. Instead, a choke insert (not shown) would be located in choke body 83. An internal tree cap (not shown) would be located at the upper end of tree 71 for sealing bore 72. A plug (not shown) would be located in profile 87. The fluid would flow out through valves 79 and 81, through the choke in choke body 83, and into a production flow line.

If the pressure of the well depletes sufficiently so as to require a booster pump, the operator would then connect a riser (not shown) to tree mandrel 89. The operator closes valves 79, 81, which along with production port 33, make up a main flow path. The operator removes the internal tree cap through the riser while leaving the crown plug within crown profile 87. With the assistance of an ROV, the operator removes the choke insert from choke body 83. The operator then removes the riser and lowers adapter 91, pressure intensifier109 and its conduits 107, 111 as a unit. Seal sub 95 will stab sealingly into tubing hanger bore 76. Connector 93 will connect adapter 91 in place. Seal sub 113 will stab sealingly into the bore of choke body 83. Connector 115 will connect outlet conduit 111 in place. A downward force due to the weight of pressure intensifier109 will pass through adapter 91 and tree 71 into wellhead housing 69.

The operator reconnects the riser at this time to adapter mandrel 103. With a wireline tool, the operator removes plug 99 from its position above lateral production port 101. The operator opens valve 97, then removes the crown plug from profile 87 and reinstalls plug 99 above production port 101. Alternately, the crown plug could be re-located from profile 87 to the position above production lateral port 101, thus serving as plug 99. The riser is removed and debris cap 105 is installed on adapter 91.

Opening valve 97 and supplying power to pressure intensifier109 causes well fluid to be flow from production bore 76 through passage 96, port 101, and conduit 107 to pressure intensifier 109. Pressure intensifier109 pumps the fluid out conduit 111 through choke body 83 into the flow line. Adapter passage 96, conduits 107, 111 and pressure intensifier 109 thus create a bypass flow path.

Pressure intensifier 109 could also operate in combination with a downhole electrical submersible pump suspended on tubing 127. If the assembly is to be used as an injection well, pressure intensifier 109 would operate in the reverse direction and fluid would flow from choke body 83 to pressure intensifier109, which pumps fluid down production passage 76.

If pressure intensifier109 is to be utilized from the beginning, it could be lowered and installed initially along with tree 71. In that instance, a T-conduit would typically be used for choke body 83. For removing pressure intensifier109 to repair or replace it, the operator attaches a riser, removes plug 99 and lowers a crown plug into crown plug profile 87. Alternately, plug 99 could be released, lowered and reset in crown plug profile 87. The operator disengages connector 115 and connector 93 and retrieves the assembly to the surface. The operator then lowers the assembly with a new or repaired pressure intensifier 109 and repeats the process.

The operator has the ability of lowering tools or instruments on wireline or coiled tubing into tubing 75 by removing debris cap 105 and connecting a riser to mandrel 103. Plug 99 is then removed through the riser, providing access for wireline tools.

Figure 4:
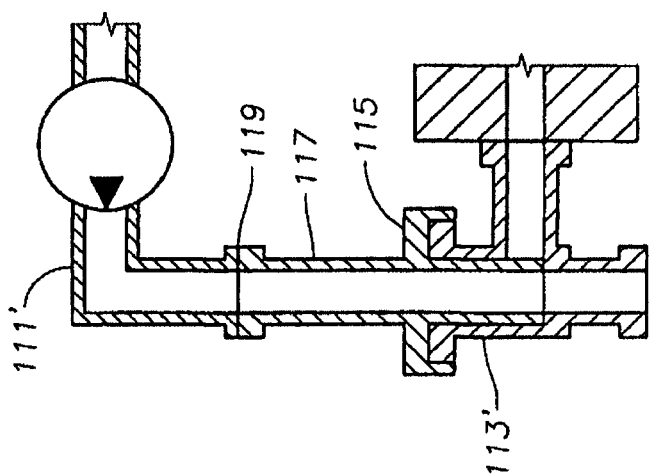
FIG. 4 is a partial view of an alternate arrangement for the mounting apparatus of FIG. 3.

FIG. 4 illustrates an alternate embodiment that is similar to FIG. 2. In this instance, seal sub 113' has a seal sub extension 117 that extends upward and terminates in a conventional subsea pipeline connector 119. Connector 115 remains secured to choke body 83. When retrieving and reinstalling pressure intensifier109, connection 119 is released and reconnected instead.

FIG. 5 illustrates a new injection well constructed in accordance with the invention. Wellhead housing 121 is the same as in FIG. 1, having a tubing hanger 123 installed therein. Tree 124 lands on wellhead housing and has seal subs 125 that communicate with a tree production bore 127 and annulus bore 129. Master valves 131, 133 and a swab valve 134 are located in the production bore 127. Annulus valves 135, 137 are located in annulus bore 129. A production port 139 extends laterally from production bore 127. Tree 124 has a mandrel 141 on its upper end that is shown with a retrievable debris cap 143.

Pressure intensifier 145 is mounted integrally to a side of tree 124 in communication with production port 139. A production wing valve, such as valve 35 of FIG. 1, is not required. Pressure intensifier 145 has an intake in communication with a flow line 147 for supplying water for injection into tubing 127. Pressure intensifier 145 may be the same type of pressure intensifier as pumps 57 (FIG. 1) and 109 (FIG. 3). However, it is not designed to be retrieved from tree 124. Rather, if maintenance or replacement is required, the well is killed and the assembly of tree 124 and pressure intensifier 145 is retrieved. While pressure intensifier 145 is shown as injecting, it could also be used in a producing well for producing well fluid.

The invention has significant advantages. Supporting the subsea pump by the mandrel of the tree utilizes the extensive strength of the tree mandrel to avoid the need for specially constructed supporting frames. The pump assembly can be readily installed and retrieved for maintenance. The assembly allows access to the tree tubing and tubing annulus for workover operations.

While the invention has been shown in only a few of its forms, it should be apparent to those skilled in the art that it is not so limited but is susceptible to various changes without departing from the scope of the invention.

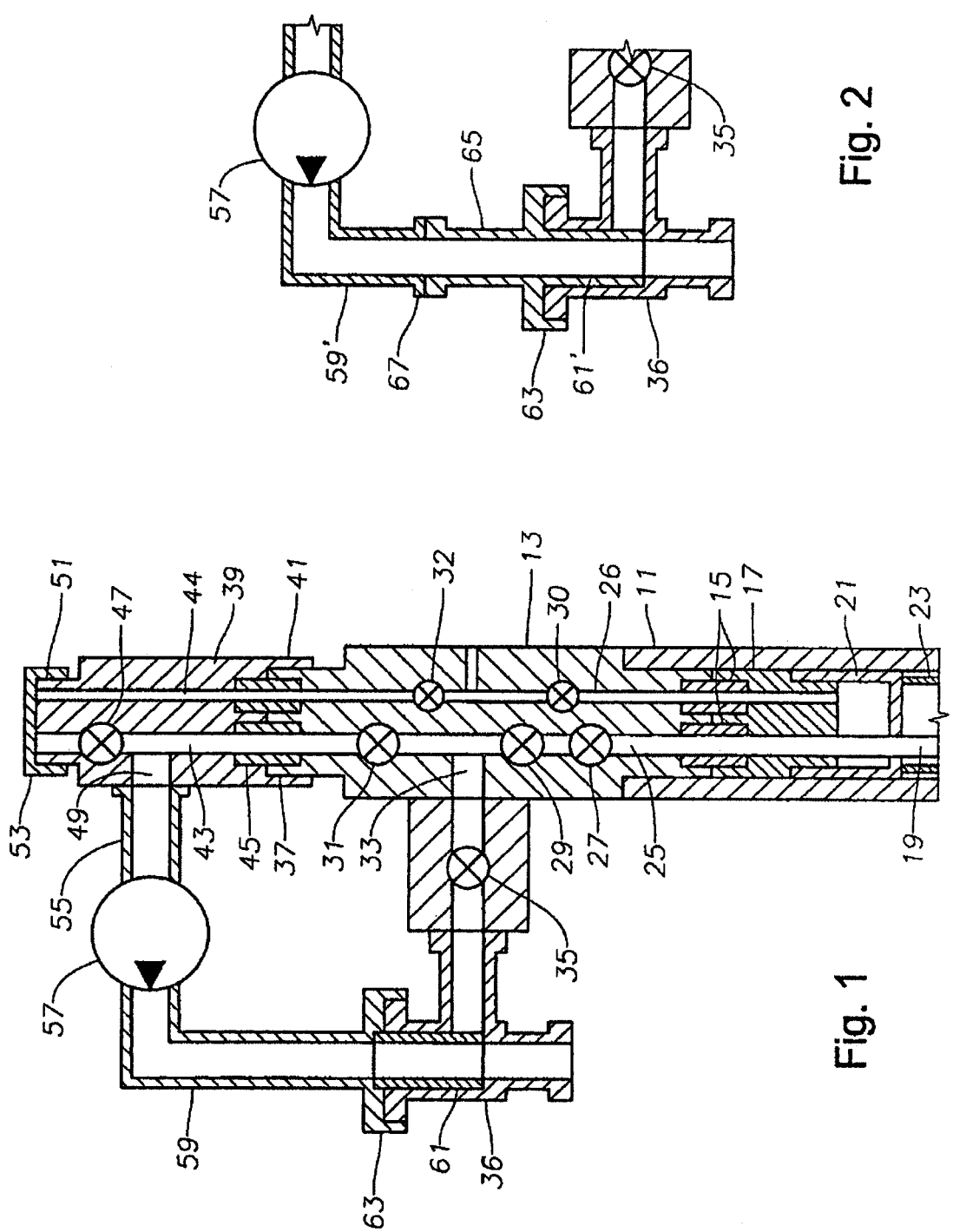

We claim:

1. A subsea well assembly, comprising:
   a subsea tree assembly having a vertical passage with laterally extending upper and lower branches, the tree assembly having a tree body with an exterior surface;
   a flow meter that is connected to the tree assembly, the flow meter having a first port connected to the upper branch and a second port;
   a tubular body mounted to the exterior surface of the tree body and alongside the tree body, the tubular body having a central cavity with a first port connected to the lower branch, a second port for connection to a flowline, and a third port;
   a conduit connected externally of the tree body between the second port of the flow meter and the third port of the tubular body; and
   a valve in the lower branch of the tree assembly, so that when closed, fluid flow through the lower branch is blocked, and fluid flows through the upper branch and the flow meter between the vertical passage in the tree assembly and the flowline.

2. A subsea well assembly, comprising:
   a subsea tree assembly having a vertical passage with laterally extending upper and lower branches;
   a flow meter that is connected to the tree assembly, the flow meter having a first port connected to the upper branch and a second port;
   a tubular body adjacent the tree assembly, the tubular body having a central cavity with a first port connected to the lower branch, a second port for connection to a flowline, and a third port;
   a conduit connected between the second port of the flow meter and the third port of the tubular body;
   a valve in the lower branch of the tree assembly, so that when closed and the flow meter is operating, fluid flows through the flow meter between the vertical passage in the tree assembly and the flowline; and wherein the tree assembly comprises:
   a tree body having an external annular profile formed on an upper portion of the tree body; and
   an adapter that lands on the upper portion of the tree body and connects to the profile, the upper branch being located within the adapter; and wherein,
   the flow meter is mounted to the adapter.

3. The well assembly according to claim 1, wherein the flow meter is laterally offset from the vertical passage to enable access from above the tree assembly to the vertical passage.

4. The well assembly according to claim 1, wherein:
   the first port of the flow meter comprises an intake of the flow meter, and the second port of the flow meter comprises an outlet of the flow meter; and
   the third port of the tubular body comprises an inlet of the tubular body, and the second port of the tubular body comprises an outlet of the tubular body, so that fluid flowing from the well up the vertical passage flows through the upper branch, the flow meter and out the second port of the tubular body into the flowline.

5. The well assembly according to claim 1, wherein the tree assembly comprises:
   an external annular profile formed on an upper portion of the tree body;
   an adapter that lands on the upper portion of the tree body and connects to the profile, the adapter having a vertical passage that registers with the vertical passage of the tree body while the adapter lands on the tree body, the flow meter being mounted to and supported by the adapter while the adapter is being lowered into engagement with the tree body; and wherein
   the upper branch of the tree assembly is located in the adapter.

6. The assembly according to claim 5, wherein:
   the vertical passage in the adapter extends to an upper end of the adapter and the flow meter is offset from the vertical passage in the adapter to provide vertical access through the adapter to the vertical passage in the tree body.

7. A subsea well assembly, comprising:
   a subsea tree body;
   an external annular profile formed on an upper portion of the tree body;
   a vertical passage extending through the tree body from a lower end of the tree body to an upper end of the tree body for communicating with a string of tubing extending into the well;
   a lateral passage in the tree body extending from the vertical passage;
   a main flow path in fluid communication with the lateral passage and extending laterally from the tree body, the main flow path having an outer end with a tubular body having a flowline port for connection to a flowline and a bypass port;
   a valve in the main flow path for selectively opening and closing communication between the flowline port of the tubular body and the lateral passage in the tree body;
   an adapter that engages the upper portion of the tree body and connects to the profile, the adapter having a passage that registers with the vertical passage of the tree body; and
   a conduit that extends externally of the tree body from the passage in the adapter to the bypass port, creating a bypass flowpath for fluid to flow between the vertical passage in the tree body and the flowline port in the tubular body when the valve in the main flow path is closed.

8. The assembly according to claim 7, wherein
   the passage in the adapter extends to an upper end of the adapter to provide vertical access through the adapter to the tubing.

9. A method of flow of fluid from a subsea tree assembly having a vertical passage that communicates with the well and a lateral passage leading outward from the vertical passage, comprising:
   (a) connecting the lateral passage to a first port on a tubular body, the tubular body having second and third ports in communication with the first port, the second port facing upwardly, the third port being connected to a flowline, one of the second and third ports being an outlet and the other of the second and third ports being an inlet;
   (b) lowering a subsea flow meter assembly having inlet and outlet conduits into the sea and connecting the flow meter assembly to the tree assembly such that the tree assembly supports the weight of the flow meter assembly and one of the conduits is connected with the vertical passage in the tree and the other of the conduits is connected to the second port of the tubular body;
   (c) blocking flow through the lateral passage and operating the flow meter assembly to measure a flow rate of fluid flowing along a flowpath between the vertical passage in the tree assembly and the flowline; and
   wherein step (b) further comprises securing the flow meter assembly to an annular grooved profile formed on an upper portion of the tree assembly.

10. The method according to claim 9 wherein step (b) further comprises connecting the inlet conduit of the flow meter assembly with the vertical passage in the tree assembly and connecting the outlet conduit of the flow meter assembly with the second port of the tubular body.

11. The method according to claim 9, wherein:
step (b) further comprises providing a vertical passage in the flow meter assembly; and the method further comprises:
lowering a tool through the vertical passages of the flow meter assembly and the tree assembly and into tubing of the well.

12. A method of flowing fluid to or from a subsea tree having an external annular profile formed on an upper portion of the tree, a vertical passage extending from a lower end of the tree to an upper end of the tree for communicating with a string of tubing extending into the well, and a lateral passage in the tree extending from the vertical passage, the method comprising:
(a) providing a main flow path with a tubular body having a flowline port and a bypass port, the main flow path being in fluid communication with the lateral passage and extending laterally from the tree, the main flow path having a valve for selectively blocking the flowline port and the bypass port from communication with the lateral passage;
(b) providing an adapter with a passage and a conduit extending from the adapter and having one end in fluid communication with the passage in the adapter; then
(c) landing the adapter on the upper portion of the tree with the passage of the adapter registering with the vertical passage in the tree and connecting the adapter to the profile;
(d) connecting the other end of the conduit to the bypass port of the tubular body, thereby defining a bypass flow path extending from the vertical passage in the tree, through the adapter and the conduit to the flowline port in the tubular body; then
(e) blocking flow through the main flow path with the valve and causing fluid flow through the bypass flow path.

13. The method according to claim 12, wherein the fluid flows in the bypass flowpath from the vertical passage in the tree to the flowline.

* * * * *

UNITED STATES PATENT AND TRADEMARK OFFICE
CERTIFICATE OF CORRECTION

PATENT NO.       : 7,740,074 B2                                                Page 1 of 5
APPLICATION NO.  : 11/595444
DATED            : June 22, 2010
INVENTOR(S)      : White et al.

It is certified that error appears in the above-identified patent and that said Letters Patent is hereby corrected as shown below:

The title page showing the illustrative figure should be deleted to be replaced with the attached title page.

The drawing sheets, consisting of Figs. 1-5, should be deleted to be replaced with the drawing sheets, consisting of Figs. 1-5, as shown on the attached pages.

Signed and Sealed this

Tenth Day of August, 2010

David J. Kappos
*Director of the United States Patent and Trademark Office*

(12) United States Patent
White et al.

(10) Patent No.: US 7,740,074 B2
(45) Date of Patent: *Jun. 22, 2010

(54) TREE MOUNTED WELL FLOW INTERFACE DEVICE

(75) Inventors: Paul W. White, Banchory (GB); Paul F. Milne, Aberdeen (GB); Norman Brammer, Aberdeen (GB)

(73) Assignee: Vetco Gray Inc., Houston, TX (US)

( * ) Notice: Subject to any disclaimer, the term of this patent is extended or adjusted under 35 U.S.C. 154(b) by 818 days.

This patent is subject to a terminal disclaimer.

(21) Appl. No.: 11/595,444

(22) Filed: Nov. 9, 2006

(65) Prior Publication Data

US 2007/0144743 A1 Jun. 28, 2007

Related U.S. Application Data

(63) Continuation of application No. 10/972,061, filed on Oct. 22, 2004, now Pat. No. 7,201,229.

(60) Provisional application No. 60/513,294, filed on Oct. 22, 2003.

(51) Int. Cl.
*E21B 7/12* (2006.01)

(52) U.S. Cl. ............... 166/347; 166/336; 166/360; 166/368; 166/250.01

(58) Field of Classification Search ............ 166/347, 166/350, 360, 368, 340, 344, 345, 68.5, 250.01, 166/336
See application file for complete search history.

(56) References Cited

U.S. PATENT DOCUMENTS

| 2,233,077 | A | | 2/1941 | Gillespie et al. | |
| 2,790,500 | A | | 4/1957 | Jones | |
| 4,099,583 | A | * | 7/1978 | Maus | 175/7 |
| 4,291,772 | A | * | 9/1981 | Beynet | 175/5 |
| 4,813,495 | A | * | 3/1989 | Leach | 175/6 |
| 5,280,766 | A | * | 1/1994 | Mohn | 166/368 |
| 5,971,077 | A | * | 10/1999 | Lilley | 166/368 |
| 6,457,529 | B2 | * | 10/2002 | Calder et al. | 166/368 |

(Continued)

FOREIGN PATENT DOCUMENTS

| WO | WO 00/70185 | 11/2000 |
| WO | WO 02/38912 A1 | 5/2002 |

*Primary Examiner*—Thomas A Beach
(74) *Attorney, Agent, or Firm*—Bracewell & Giuliani

(57) ABSTRACT

A subsea production tree has an external annular profile formed on an upper portion of the tree. A vertical passage extending from a lower end of the tree to an upper end of the tree for communicating with a string of tubing extending into the well. A lateral passage in the tree extending from the vertical passage. A flow path in fluid communication with the lateral passage extends laterally from the tree, the flow path having an upward facing receptacle. An adapter lands on the upper portion of the tree and connects to the profile, the adapter having a passage that registers with the vertical passage of the tree while the adapter lands on the tree. A flow interface device mounts to and lands with the adapter, the flow interface device having an inlet conduit and an outlet conduit, one of the conduits being connected to the passage in the adapter, the other of the conduits stabbing into sealing engagement with the receptacle as the adapter lands on the tree.

13 Claims, 3 Drawing Sheets

Fig. 3